US012161576B2

(12) United States Patent
Schiermeister et al.

(10) Patent No.: US 12,161,576 B2
(45) Date of Patent: Dec. 10, 2024

(54) BACK SUPPORT BELT

(71) Applicant: Bauerfeind AG, Zeulenroda-Triebes (DE)

(72) Inventors: Linda Schiermeister, Bad Homburg (DE); Toni Holter, Chemnitz (DE); Hans B. Bauerfeind, Zeulenroda-Triebes (DE)

(73) Assignee: Bauerfeind AG, Zeulenroda-Triebes (DE)

( * ) Notice: Subject to any disclaimer, the term of this patent is extended or adjusted under 35 U.S.C. 154(b) by 693 days.

(21) Appl. No.: 17/259,066

(22) PCT Filed: Jul. 2, 2019

(86) PCT No.: PCT/EP2019/067766
§ 371 (c)(1),
(2) Date: Jan. 8, 2021

(87) PCT Pub. No.: WO2020/011604
PCT Pub. Date: Jan. 16, 2020

(65) Prior Publication Data
US 2021/0177638 A1 Jun. 17, 2021

(30) Foreign Application Priority Data
Jul. 10, 2018 (DE) .......................... 102018211431.5

(51) Int. Cl.
*A61F 5/02* (2006.01)
(52) U.S. Cl.
CPC .............. *A61F 5/028* (2013.01); *A61F 5/026* (2013.01)

(58) Field of Classification Search
CPC .. A61F 5/028; A61F 5/026; A61F 2005/0197; A61F 5/02; A61F 5/30;
(Continued)

(56) References Cited

U.S. PATENT DOCUMENTS 5,499,965 A 3/1996 Sanchez
9,125,442 B2 9/2015 Brown
(Continued)

FOREIGN PATENT DOCUMENTS

CA 3012897 A1 8/2017
DE 202014009385 U1 1/2015
(Continued)

OTHER PUBLICATIONS

Office Action for JP Application No. 2021-500557 dated Aug. 31, 2021, 2 pages, English translation.
(Continued)

*Primary Examiner* — Keri J Nelson
(74) *Attorney, Agent, or Firm* — Sheppard Mullin Richter & Hampton LLP

(57) ABSTRACT

The invention relates to a back support belt system, in particular a back orthosis or reclination orthosis for the treatment and prevention of back problems. The system comprises a pelvis strap and two independent left and right shoulder straps extending therefrom, those shoulder straps crossing each other in the back and ribcage region and being connected to the pelvis strap via tension straps, for simultaneously tensioning the pelvis strap and the shoulder straps.

15 Claims, 9 Drawing Sheets

Figure 1:
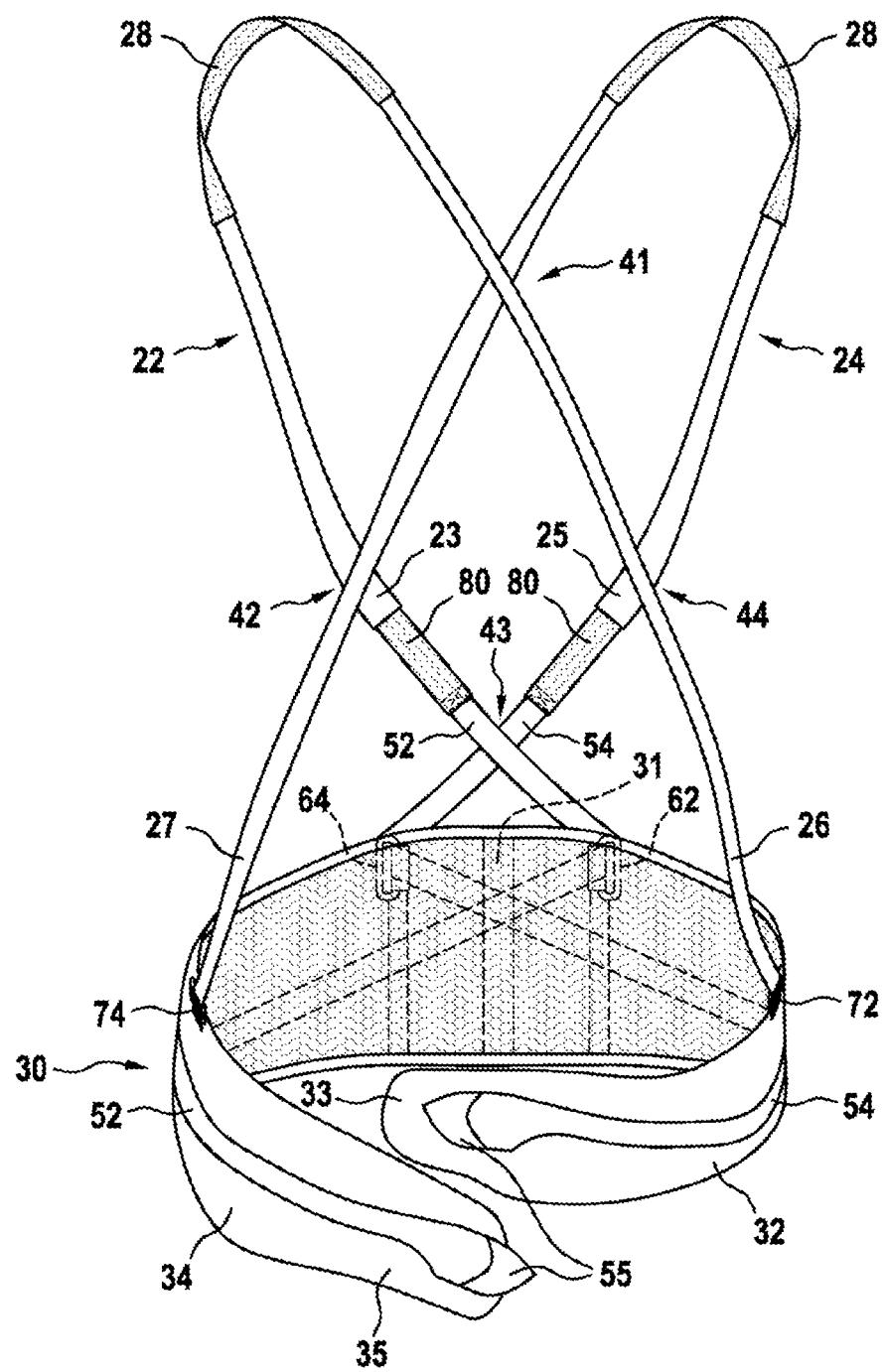

(58) Field of Classification Search
CPC .... A61F 5/32; A41D 1/02; A41D 1/04; A41D 13/0525
See application file for complete search history.

(56) References Cited

U.S. PATENT DOCUMENTS

| | | |
|---|---|---|
| 2004/0193082 A1 | 9/2004 | Cofre |
| 2010/0318010 A1* | 12/2010 | Sandifer ................. A61F 5/026 602/19 |
| 2012/0245501 A1* | 9/2012 | Rossi ...................... A61F 5/026 602/19 |
| 2013/0012853 A1 | 1/2013 | Brown |
| 2013/0090585 A1 | 4/2013 | Bue, Jr. et al. |
| 2017/0273365 A1* | 9/2017 | Muhlenfeld ............. A41B 1/08 |
| 2019/0046115 A1* | 2/2019 | Richardson ............. G01N 3/08 |

FOREIGN PATENT DOCUMENTS

| | | |
|---|---|---|
| JP | 11104159 A | 4/1999 |
| JP | 11313846 A | 11/1999 |
| JP | 2001218779 A | 8/2001 |
| JP | 2001224613 A | 8/2001 |
| JP | 2011062245 A | 3/2011 |
| WO | 2017196887 A1 | 11/2017 |
| WO | 20170196884 A1 | 11/2017 |

OTHER PUBLICATIONS

English translation of the International Preliminary Report on Patentability for PCT/EP2019/067766 dated Nov. 11, 2020, 10 pages.
English translation of International Preliminary Report on Patentability for PCT/EP2019/067766 dated Nov. 11, 2020, 10 pages.
English translation of International Search Report and Written Opinion for PCT/EP2019/067766 dated Sep. 4, 2019, 15 pages.

* cited by examiner

BACK SUPPORT BELT

CROSS REFERENCE TO RELATED APPLICATIONS

This application is a U.S. National Stage Application under 35 U.S.C. 371 of International Application No. PCT/EP2019/067766, filed Jul. 2, 2019, which claims priority to German Patent Application No. 10 2018 211 431.5, filed Jul. 10, 2018. The contents of each of the aforementioned are hereby incorporated by reference in their entirety into the present disclosure.

The invention relates to a back support belt system, in particular a back orthosis or reclination orthosis for the treatment and prevention of back problems. The system comprises a pelvis strap and two independent left and right shoulder straps extending therefrom, those shoulder straps crossing each other in the back and ribcage region and being connected to the pelvis strap via tension straps, for simultaneously tensioning the pelvis strap and the shoulder straps.

Back support belt systems are used to straighten the upper body, i.e., for the treatment and correction of bad postures and curved spines, for example, in the case of osteoporosis. Known back support belt systems and orthoses essentially consist of a pelvis strap, which can be closed under tension over the pelvis or hip of a patient, or generally a wearer, and which is then intended to form a basis for the application of force on the back. Known systems also contain straps or support rails which extend from the pelvis strap and which are intended to reposition or support the shoulders in spatial relation to the spine or the upper spine portion in relation to the lower spine portion through a targeted application of force. Through the interaction of these elements, the spine of the wearer is supposed to be mechanically stabilized and, above all, straightened in the region of the shoulder and the upper thoracic spine. The more the shoulder straps are tensioned, the more the shoulders are supposed to be pulled back, by means of which the upper body can be straightened.

Back support belt systems are also intended to help reduce stress on the back when lifting and carrying loads, in particular avoiding excessive stress, in that the forces generated especially in the region of the shoulders are purposefully absorbed and distributed. When lifting and carrying loads, support belts are intended to introduce the forces acting primarily on the upper body via arms and shoulders directly into the pelvis or the torso. In this way, the spine is supposed to be bypassed and relieved. In addition, a back support belt system is intended to remind the wearer to assume a harmful, burdensome relieving posture in the case of an excessive poor posture of the upper body, and to convey a feeling of safety and stabilization. Back support belt systems are thus also intended for the occupational safety of healthy people. At the same time, the back support belts are supposed to guide and limit the movement in a controlled manner in order to avoid bad postures unfavorable for the back when lifting or carrying loads. This is expedient in occupational safety, rehabilitation and certain sporting activities.

The disadvantage of known back support belt systems or back orthoses of this type is the complex structure, which makes it difficult for the wearer to apply and why incorrect use can hardly be ruled out. The mostly rigid design of known bandages with support elements and straps helps to achieve a support effect, but an individual adaptation to the specific indication situation, to the specific therapy requirement and/or to the anatomical circumstances of a wearer is not possible to a sufficient extent. Particularly a movement of the user results in certain movement phases, in the case of particular stress or even when tensioning the back support belt system during application or afterwards, in an unwanted slipping of the support belt system on the body (migration) to a position that greatly affects the wearing comfort and can render the orthosis essentially ineffective. In particular, patients with restricted mobility find it difficult in practice to apply such belt systems and to generate the necessary tension on the support elements and on the pelvis strap even after they have been applied. It can also be difficult to apply an orthosis that has already been set up for the purpose of sufficient support, i.e., a pretensioned orthosis, under said tension. Pretensioned shoulder straps can pull a pelvis strap, to which they are connected, unfavorably upwards, particularly into the upper waist portion in the direction of the lower ribcage, even during application, so that a functional fit on the pelvis can no longer be achieved.

Therefore, the technical problem addressed by the invention is that of improving such back support belt systems or back orthoses, such as reclination orthoses, which are based at least on a basic structure containing a pelvis strap frame with force-introducing shoulder straps extending therefrom, so that it is easier to apply them to the wearer and in addition, a migration of the system, especially of the pelvis frame, is effectively prevented as soon as it is applied or during use, especially during a movement of the wearer. As a result, the support and relief effect of such systems is supposed to be improved and can also be maintained over the entire duration of wear.

The technical problem is completely solved by the new type of back support belt or back orthosis design according to the claims. Said back orthosis or back support belt system comprises at least the following elements: An at least in portions stretchable pelvis strap to be applied around the pelvis of a wearer, having a middle portion that can be positioned in the lumbar/sacral region in the applied state and left and right side portions that extend laterally therefrom and pull ventrally when applied, a right shoulder strap loop which, according to the invention, extends solely from said left side portion of the pelvis strap to be applied over the right shoulder of the wearer, and a left shoulder strap loop which, according to the invention, extends solely from said right side portion of the pelvis strap to be applied over the left shoulder of the wearer. It is therefore provided that both ends of a shoulder strap loop begin on the opposite (contralateral) pelvic strap side, i.e., they cross the torso of the wearer on both the back (dorsally) and in the abdomen or chest region of the wearer. In this case, it is particularly provided that the right shoulder strap loop and the left shoulder strap loop cross each other in the applied state in a dorsal central upper crossing point, in a dorsal central lower crossing point in the applied state and particularly also in two lateral crossing points in the applied state, particularly in the region of the ribcage or the waist.

According to the invention, said two shoulder strap loops are each connected at their at least one end to the pelvis strap via a, preferably inelastic, tension strap that, via at least one first deflection element, runs to the respective side portion of the pelvis strap and is deflected, so that it runs along on or even in the pelvis strap in a sliding manner to the respective pelvis strap end, i.e., to the ventral portion when the orthosis is applied. The tension strap—and thus the respective shoulder strap loop connected thereto—can be tensioned and, in particular, can be fixed at the respective pelvis strap end.

Therefore, in a first aspect of the invention, a back orthosis is provided, comprising: a stretchable pelvis strap to be applied to the pelvis of a wearer, having a middle portion that can be positioned in the lumbar/sacral region in the applied state and a left side portion extending laterally therefrom with a left pelvis strap end and a right side portion extending laterally therefrom with a right pelvis strap end, wherein the pelvis strap ends are connectable to each other under tension for application; a right shoulder strap loop to be applied over the right shoulder of the wearer, which is connected via both its first end and also its second end alone, i.e., exclusively, to the left side portion of the pelvis strap; a left shoulder strap loop to be applied over the left shoulder of the wearer, which is connected via both its first end and also its second end alone to the right side portion of the pelvis strap; wherein the right and left shoulder strap loop are each connected at least at their respective first ends to the pelvis strap via a first tension strap, and wherein the first tension strap of the right shoulder strap loop runs via at least one first left deflection element which is arranged on the left side portion and runs along on or in the pelvis strap towards a pelvis strap end in a sliding manner, where it can be tensioned and fixed thereto, and wherein the first tension strap of the left shoulder strap loop runs via at least one first right deflection element which is arranged on the right side portion and runs along on or in the pelvis strap towards a pelvis strap end in a sliding manner, where it can be tensioned and fixed thereto.

For this purpose, it is provided in a first embodiment that the first tension strap of the right shoulder strap loop runs via at least a first left deflection element which is arranged on the left side portion, crosses the middle portion and runs along on or in the right side portion of the pelvis strap towards the right pelvis strap end in a sliding manner, and wherein the first tension strap of the left shoulder strap loop runs at least via a first right deflection element on the right side portion, crosses the middle portion and runs along on or in the left side portion of the pelvis strap towards the left pelvis strap end in a sliding manner.

In a further embodiment alternative to the first embodiment, it is provided that the first tension strap of the right shoulder strap loop runs via the at least one first left deflection element, which is arranged on the left side portion, and runs from the first left deflection element in the direction of the middle portion to at least one second left deflection element arranged on the middle portion and from there, runs along the left side portion towards the left pelvis strap end, and wherein the first tension strap of the left shoulder strap loop runs via the at least one first right deflection element, which is arranged on the right side portion, and runs from the at least one first right deflection element in the direction of the middle portion to at least one second right deflection element arranged on the middle portion and from there, runs along the right side portion towards the right pelvis strap end.

According to the invention, "tension strap" primarily refers to an essentially inelastic, i.e., tensile-resistant, flexible strap in the form of a woven belt. Functionally equivalent designs, such as chain or link belts, straps made from solid material of flexible polymers and metal bands are also included herein. Alternatively, it also refers to tension ropes or tension cords, individually or in a combination of parallel or interwoven cords. In particular, it is provided that the tension straps, particularly in comparison to the shoulder straps, are not stretchable, i.e., essentially inelastic and tensile-resistant.

According to the invention, "deflection element" refers primarily to an eyelet or ring for a strap or a rope to be guided through, but also to a mounted roller or roller block. An anti-slip or a slip-improving coating can be provided, depending on the focus of the application and the specific tension strap guide (see below).

In the present case, "wearer" refers to a person who applies and uses, i.e., wears, the belt system according to the invention, for example, as part of occupational safety measures in order to prevent excessive stress or poor posture when working, especially when carrying loads. It also refers to a patient who applies and uses, i.e., wears, the belt system according to the invention, for example, as part of therapeutic measures in order to counteract excessive stress or incorrect posture of a previously damaged, diseased musculoskeletal system or to allow for a targeted movement guidance in the sense of therapy for the diseased musculoskeletal system.

According to the invention, the tension straps are guided on or in the pelvis strap along its longitudinal extension such that the shoulder strap loops can be tensioned, i.e., respectively facilitated by said tension straps, when the pelvis strap is stretched, in particular while the orthosis is applied to the wearer or afterwards. It is particularly provided that, when they are in the applied state, the shoulder strap loops can be tensioned separately on the pelvis strap via the tension straps.

It is also provided that, by tensioning the shoulder straps on the pelvis strap, i.e., the respective tension straps connected to the shoulder strap loops, in particular while the orthosis is applied to the wearer or afterwards, the pelvis strap itself is also tensioned, i.e., can also be tensioned further.

According to the first embodiments, the pelvis strap is advantageously also tensioned together with the tensioning of the shoulder strap because the two lateral and central deflection points move towards one another due to the tension on the tension strap. In the second embodiment, the pelvis strap and the shoulder strap can be tensioned separately. This is especially also possible for elderly patients with restricted mobility. Since particularly the ends of the tension straps of the shoulder straps can each be fixed directly to the pelvis strap, for example, by means of Velcro elements and/or can be tensioned there by separate tensioning devices on the side portions, a quick and easy adjustment of the shoulder strap tension is possible even while the back support belt system according to the invention is worn.

If the pelvis strap is applied under tension around the pelvis or hip of the wearer by closing the two pelvis strap ends, especially in the region of the abdomen of the wearer, the pelvis strap, according to this aspect of the invention, can be tensioned or tightened further in that tension is applied to the tension straps of the shoulder strap loops guided along the pelvis strap according to the invention in order to tension the shoulder straps. It has been shown that the tension of the pelvis strap can increase proportionally to the increase in shoulder strap tension, which results in a better fit and a better hold of the pelvis strap. An unwanted migration of the pelvis strap when tensioning the shoulder straps can thus be avoided.

For this purpose, it is particularly provided that the tension straps each have free tension strap ends which can be fixed directly to the respective pelvis strap ends for tensioning. This can be achieved in an inherently known manner using releasable connecting elements. Hooks and eyelets or, alternatively or additionally, Velcro hooks, in particular on the side of the free tension strap ends, and Velcro counter elements, especially velour, in particular on the side of the pelvis strap end, are preferred. A location-variable positionability of the tension strap ends at or on the pelvis strap ends is preferred in order to make the tension and direction of tension individually adaptable. This is achieved in particular by means of large surfaces formed on the pelvis strap ends, having Velcro counter elements, or by a plurality of surfaces spaced apart from one another.

The invention thus particularly allows for a practically two-step tensioning when applying or using the orthosis: Once the pelvis strap ends are closed, possibly under initial tension, the pelvis strap can be tightened further in a first tensioning process using the free tension strap ends; in this first step, the tension introduction preferably first leads to a tension that runs radially around the hip or the pelvis of the wearer, thus applying the pelvis strap in a better and tighter manner. In a second step of the tensioning process, the two shoulder strap loops can be re-tensioned via the two other laterally lying free tension strap ends. Both tensioning processes can be carried out simultaneously in one tensioning step, or in several separate tensioning steps that can be distinguished noticeably by exertion of force and/or tensioning effect on the pelvis and shoulder straps, in particular on the basis of the specific arrangement and guidance of the tension straps and the deflection elements on the pelvis strap and on the basis of the static and sliding friction conditions of the fixed or running straps on the deflection elements and along the pelvis strap.

Due to the dynamic force distribution of the shoulder straps on the pelvis strap, which is made possible in particular due to the slidingly guided tension straps of the shoulder straps, the tension force can advantageously be distributed dynamically in the back orthosis depending on the state of movement of the wearer, without resulting in local excessive tension and thus unwanted migration of the back orthosis. In particular, the arrangement according to the invention allows for the tensioning force, which holds the pelvis strap through static friction on the pelvis or iliac crest of the wearer, to be in an appropriate and always adjusted relationship with the tensioning force of the shoulder straps, whereby excessive tension of the shoulder straps, which reduces the holding force of the pelvis strap (static friction), can be effectively avoided. As a result, an unwanted migration of the pelvis strap and thus the back orthosis is prevented.

In this case, it is advantageously also made possible that, when applied to the wearer, the elastic pelvis strap is stretched for tensioning and closing the two side portions, whereby the tension straps, particularly in the form of tension belts and/or tension ropes or tension cords, which run along the pelvis strap, particularly between the respective side portion and the central pelvis strap portion, are simultaneously also stretched on both sides, so that the shoulder straps are automatically tensioned in relation to the pelvis strap when the pelvis strap is applied and the two strap ends are closed under tension, whereby the necessary tension is easily generated, which allows particularly for the force introduction on the shoulders required for reclination.

Each tension strap is individually guided on or in the pelvis strap between at least one central deflection element in the region of the dorsal middle portion of the pelvis strap and at least one lateral deflection element which is arranged in the lateral region located further towards the front (ventrally) of the respective side portions. For the dynamic tensile force distribution according to the invention in the orthosis, the course and arrangement of the tension straps on the pelvis strap are particularly decisive for the desired function of the belt system in the orthosis. It can be selected on the basis of the intended use, therapy objective or requirements of the wearer. In one case, a particularly relieving effect of the shoulder straps, for example, when used in the field of occupational safety, is intended, and in another case, an effective and easily appliable reclination orthosis is desired for osteoporosis patients with restricted mobility. The present invention therefore comprises several variants and designs of the tension strap guides.

In a first variant, the tension strap that comes from the dorsal first end of the right shoulder strap loop runs from a first left deflection element positioned to the left of the middle portion along the left side portion to the left pelvis strap end, and the tension strap that comes from the dorsal first end of the left shoulder strap loop runs from a first right deflection element positioned to the right of the middle portion along the right side portion to the right pelvis strap end. This means that the incoming tension strap of the opposite shoulder strap loop is guided directly towards the front (ventrally) solely via a lateral deflection element.

In another variant, said tension strap, coming from the dorsal first end of the right shoulder strap loop, runs from a first left deflection element at a distance further from the middle portion along the left side portion in the direction of the middle portion to a second left deflection element at a distance closer to the middle portion and from there, runs along the left side portion towards the left pelvis strap end, and the tension strap, coming from the dorsal first end of the left shoulder strap loop, runs from a first right deflection element at a distance further from the middle portion along the right side portion in the direction of the middle portion to a second right deflection element at a distance closer to the middle portion and from there along the right side portion towards the left pelvis strap end.

This means that each tension strap is guided between the at least one central deflection element and the at least one lateral deflection element. In a first variant, the tension strap coming in a traversing manner from the shoulder strap loop of the opposite body half is guided on the lateral deflection element in the direction of the middle portion of the pelvis strap and from there onto the deflection element located closer to the center. From the more central deflection element, the tension strap is guided towards the front (ventrally) on the same side of the pelvis strap. In another variant, the incoming tension strap is guided back and forth several times in a direction-changing manner on a plurality of lateral deflection elements and at least one more centrally located deflection element, particularly in the manner of a waist, wherein the deflection elements form the blocks and the tension strap each forms the runner.

With the applied pelvis strap, the place of introduction of the tension straps of the shoulder straps lies in the back/dorsal region of the pelvis strap but always between the middle portion and the aforementioned lateral portion. For this purpose, the deflection elements are guided on or in the region of stretchable (elastic) portions of the pelvis strap such that an active change in length of the pelvis strap through pull or tension leads to pull or tension on the tension strap, thus effectively shortening its length. In a particularly preferred embodiment, the tension strap is in this case guided back from a lateral pelvis strap portion to a more central pelvis strap portion and from there guided back again in the direction along the lateral pelvic portion. With this "Z"-shaped deflection of the tension straps, a force/length transfer is achieved in the manner of a single or possibly multiple pulley. Simply pulling on the shoulder strap, for example, when bending, results in a two-fold or manifold increase of the tension on the pelvis strap. Conversely, the pull on the pelvis strap when applied leads to a dual or multiple effective shortening of the shoulder strap. The latter is particularly advantageous for applying the back strap system according to the invention because particularly the shoulder straps can at first be applied loosely and then shortened to an expediently large extent by the tensioning when the pelvis strap is applied in order to achieve the intended support function.

In preferred embodiments, it is additionally provided that the first, outer starting point of the shoulder strap end is positioned in the region of the iliac crest, preferably exactly on the iliac crest (crista iliaca), when the pelvis strap is in its applied state. This advantageously ensures that the second end of the respective shoulder strap loop attached to the pelvis strap, i.e., in the anatomical frontal plane of the body of the wearer or user, does not experience any significant passive change in length when moving, especially when bending the back. In combination with the specific course of the shoulder straps according to the invention on the body, a "neutral point" is achieved which prevents unwanted additional transverse forces during movement, which could additionally cause the migration of the pelvis strap. The front point of introduction of the tensile force of the respective shoulder strap loop in the pelvis strap lies therefore preferably in the anatomical frontal plane. The belt system thus retains its tension even during bending.

In a first variant thereof, the second end of the right and left shoulder strap loops is each connected at left and right lateral anchors, respectively, to the respective side portions, wherein, in the applied state of the pelvis strap, the left and right lateral anchors are each located on or in the region of the left and right iliac crest of the wearer. Said second ends of the shoulder strap loops can be connected to said anchors either directly or indirectly via, in particular length-adjustable, stationary tension straps. For this purpose, such tension straps can be guided in an inherently known manner through eyelets serving as anchors and be clamped with themselves in a buckle for the purpose of length adjustment.

In another variant thereof, the second end of the right and left shoulder strap loops is connected to the pelvis strap via a second tension strap, wherein the second tension strap of the right shoulder strap loop runs slidingly via at least one left lateral deflection element along the left side portion towards the left pelvis strap end, and the second tension strap of the left shoulder strap loop runs slidingly via at least one left lateral deflection element along the left side portion towards the left pelvis strap end, and wherein the left and right lateral deflection elements in the applied state of the pelvis strap are each located on or in the region of the left and right iliac crest of the wearer.

In preferred embodiments of the invention, at least one end of the shoulder strap loop, which forms the transition between the shoulder strap and the associated tension strap, is designed as a particularly elastic strap portion.

According to the invention, "elastic strap portion" refers primarily to an elastic band, i.e., a flexible band, particularly in the form of a woven belt, that can be stretched by tensile stress. Functionally equivalent designs, particularly elastomer strips, preferably made of rubber, silicone rubber, polyurethane, and the like, are thus also included. Alternatively, this also refers to elastic tensioning ropes with inserts made of elastomeric fibers. It is provided that said elastic strap portions, particularly in comparison to the other portions of the shoulder strap loops, are more elastic, i.e., they can be stretched further under tensile stress. In a preferred variant, said elastic strap portions are the only components of the shoulder straps that are stretched, i.e., lengthened, under the tensile forces that can occur when the orthosis is used properly, especially when bending the back. The elastic strap portion preferably has a force-expansion range at a longitudinal expansion of +60% from 7 N to 55 N, in particular from 20 N to 40 N.

This elastic strap portion is preferably arranged at the end of the shoulder strap loop that pulls upwards over the rear upper back to the shoulders. Since the change in length when the back is bent is particularly pronounced in this region of the body, the particularly elastic strap portion located in said region can reduce excessive tension on the straps, i.e., compensate for it through its intrinsic stretching during bending. Due to its elasticity, the elastic strap portion is used to limit the tensile force of the tension introduced into the pelvis strap by the shoulder straps, which prevents the pelvis strap from migrating. In addition, the change in length of the back during bending can also be compensated, which holds the shoulder straps in position on the shoulder, provides freedom of movement and increases the wear comfort and effectiveness of the back belt system.

In a variant thereof, said elastic end portion is additionally provided with a separately formed mechanical expansion limiter that is guided parallel to the elastic portion. The expansion limiter can be designed as at least one less elastic or inelastic band which is connected to the respective ends of the elastic portion. Depending on the desired therapy objective or intended use of the system, this can be used for a controlled motion control during bending. In particular, excessive bending of the back is supposed to be prevented, which may be indicated therapeutically, for example, in postoperative rehabilitation or in the field of occupational safety when lifting loads, for reclination and postural improvement and the resulting improvement in load transfer in the back.

In a further embodiment, the support belt system according to the invention is guided in separate cross guides at least at the crossing points of the shoulder strap loops. This is used in particular to simplify the application of the back orthosis to the wearer or user because the cross guides hold the intersecting shoulder straps in the correct positions. At least one such cross guide is preferably provided in the upper, central, rear crossing point.

The back support belt system according to the invention allows for the wearer to be reminded in the case of an incorrect posture of the upper body, i.e., in particular: Greatly forward bent torso and in the worst case additional rotation of the back in the bent position, to adopt a gentler posture, i.e., in particular: an upright posture. When lifting loads with a curved spine, the load is shifted to the front part of the ventral pillar of the vertebral body; by straightening the spine and lifting from the knees (upright posture), the load is advantageously distributed over the entire region of the ventral pillar. The upright posture can be assumed by the wearer particularly when said wearer experiences an increased pull via the shoulder strap system according to the invention when the upper body is bent forwards. In this case, the pelvis strap acts as an "anchor" and establishes the central fixed point which is used to generate a force from the movement on the shoulders in the dorsal direction via the belt system. A further side effect of the tightly fitting, tensioned pelvis strap of the back support belt system according to the invention is the conveying of a feeling of safety and stabilization to the wearer of the system.

In a particular embodiment, the back support belt system according to the invention is therefore fitted onto an elastic vest or jacket, wherein the shoulder straps and/or the pelvis strap are fixed at least in portions to the vest or jacket. The subject matter of the invention is therefore also protective clothing, particularly in the form of a vest or jacket, containing a stretchable vest or jacket and the herein described back support belt system according to the invention.

In the simplest case, the back support belt system is sewn to the vest or jacket. In an alternative variant, the support straps are guided in loops on the vest or jacket. The design on a vest or jacket allows for a simplified application and removal, which is very useful particularly for short-term and recurring use of the back support belt system, for example, in the field of occupational safety. The vest or jacket used is made of elastic fabric or knitted fabric. Alternatively, flexible vests, such as those inherently known as safety vests, can be fitted with the back support belt system according to the invention.

Finally, the subject matter of the invention is also the use of the back orthosis according to the invention or the protective clothing according to the invention for protection against adverse stresses on the back.

The invention is illustrated in more detail by the following specific embodiments, wherein said embodiments are not meant to be limiting.

FIG. 1 is a perspective front view of a first embodiment of the back orthosis according to the invention. A left shoulder loop 24 that can be applied over the left shoulder is attached to a pelvis strap 30 with a rear middle portion 31 on the right side portion 34 of the pelvis strap 30, and a right shoulder loop 22 that can be applied over the right shoulder is attached to the left side portion 32 of the pelvis strap 30. The (dorsal) end 25 of the left shoulder strap loop 24, which, in the applied state, runs on the back, is connected via an elastic strap portion 80 to an essentially inelastic tension strap 54. The tension strap 54 runs via a right deflection element 64, designed in this embodiment as an eyelet, a ring or a simple buckle, to the right of the middle portion 31 on the pelvis strap 30 and, crossing the middle portion 31, is guided towards the front along the left side portion 32 of the pelvis strap 30 where it ends in a free end 55. In this case, the free end 55 of the tension strap 54 can be fixed to the left pelvis strap end 32. Correspondingly symmetrical thereto, the rear end 23 of the right shoulder strap loop 22 runs via an elastic strap portion 80 to a tension strap 52, which runs via a corresponding left deflection element 62 to the pelvis strap 30, also crosses the middle portion 31 and runs along the right side portion 34 to end in a free end 55. The free end 55 of the tension strap 52 can be fixed to the right pelvis strap end 35. The respective other ends 26, 27 of the shoulder strap loops 22, 24 are firmly connected in the illustrated embodiment to a region of the side portions 32, 34, which lies further to the side, i.e., further away from the middle portion 31. For this purpose, the second end 26 of the right shoulder strap loop 22 is firmly connected to the left side portion 32 of the pelvis strap 30 at a left anchor 72. Said left anchor 72 is positioned in a region of the left side portion 32, which, when the orthosis is applied to the wearer, lies on or above the left iliac crest of the wearer. The second end 27 of the left shoulder strap loop is also firmly connected to the right side portion 34 of the pelvis strap 30 via a right anchor 74. Said right anchor 74 is also positioned in a region of the right side portion 34, which, when the orthosis is applied to the wearer, lies on or above the right iliac crest of the wearer. Due to the positioning, according to the invention, of the fastenings of the ends 23, 25, 26, 27 of the shoulder strap loops 22, 24 on the pelvis strap 30 on the opposite side of the body, the shoulder strap loops cross each other at four crossing points: a rear central upper crossing point 41 and a rear central lower crossing point 43 and in a left lateral crossing point 42 and a right lateral crossing point 44. On the upper portions of the shoulder straps which, when the orthosis is applied to the wearer, run in the region of the clavicle and the shoulder blade, additional, in particular partially elastic and/or padded, shoulder straps 28 are optionally formed.

Figure 2:
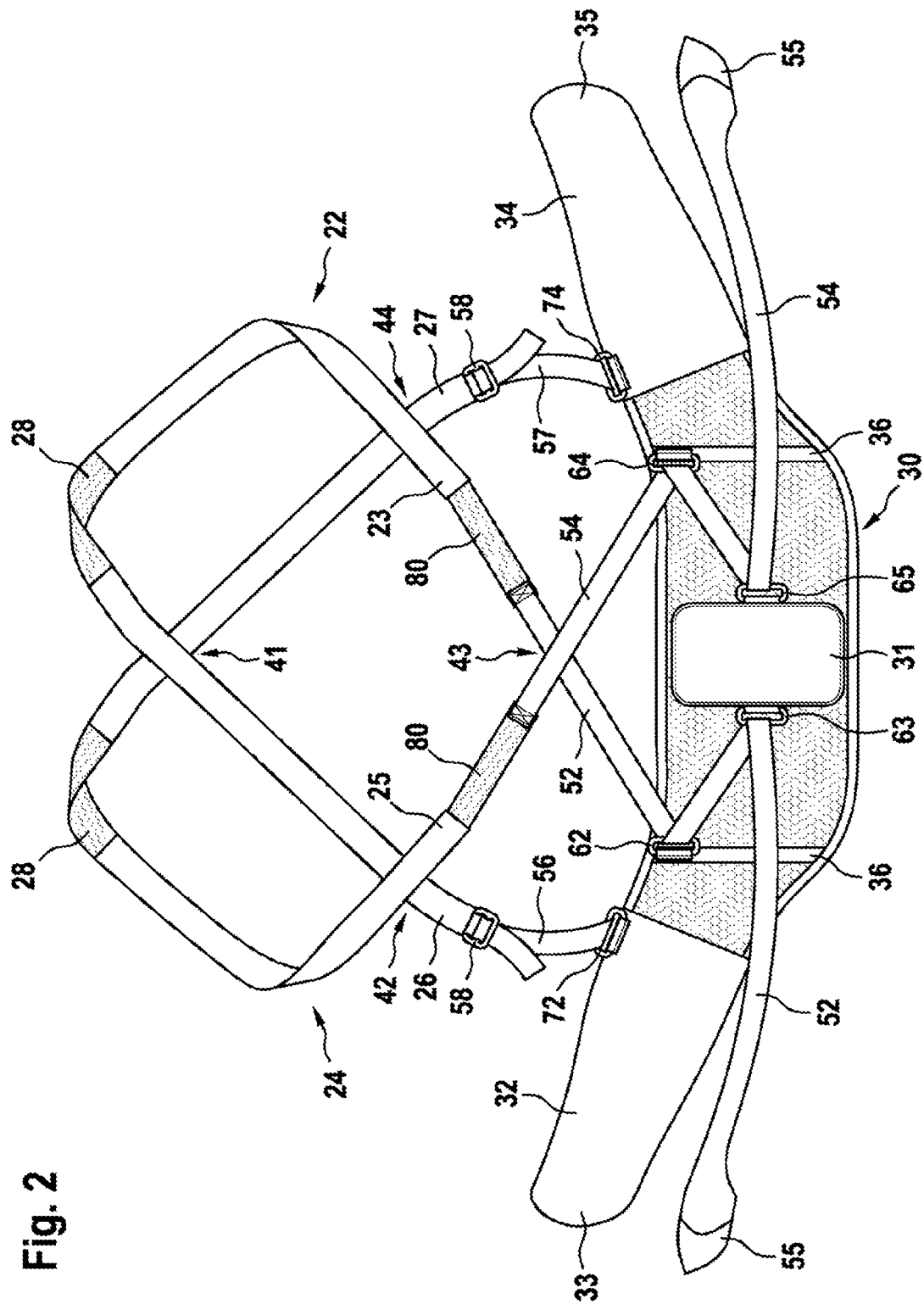

FIG. 2 is a perspective rear view of another embodiment of the back orthosis according to the invention in the open state. Deviating from the components corresponding to the features shown in FIG. 1, the embodiment according to FIG. 2 has, in addition to otherwise corresponding components, an alternative tension strap guide: The tension straps 52, 54 of the right and left shoulder strap loops 24, 22 enter the pelvis strap 30 in first lateral left and right deflection elements 62 and 64, respectively. From there, they are first deflected in the direction of the middle portion 31 and there, they enter second left and right deflection elements 63, 65 positioned centrally, i.e., closer to the middle portion 31. There, the tension straps 52 and 54 are deflected and subsequently pull in the direction of the left and right pelvis strap end 33, 35, respectively. In addition to the embodiment of FIG. 1, adjustable second tension straps 56, 57 are provided in the embodiment according to FIG. 2 for fastening the respective second end 26, 27 of the shoulder strap loops 22 and 24 at the anchor points 72 and 74, each of which is in this case clamped with itself in buckles 58 in order to achieve a length adjustment of the shoulder straps.

Figure 3:
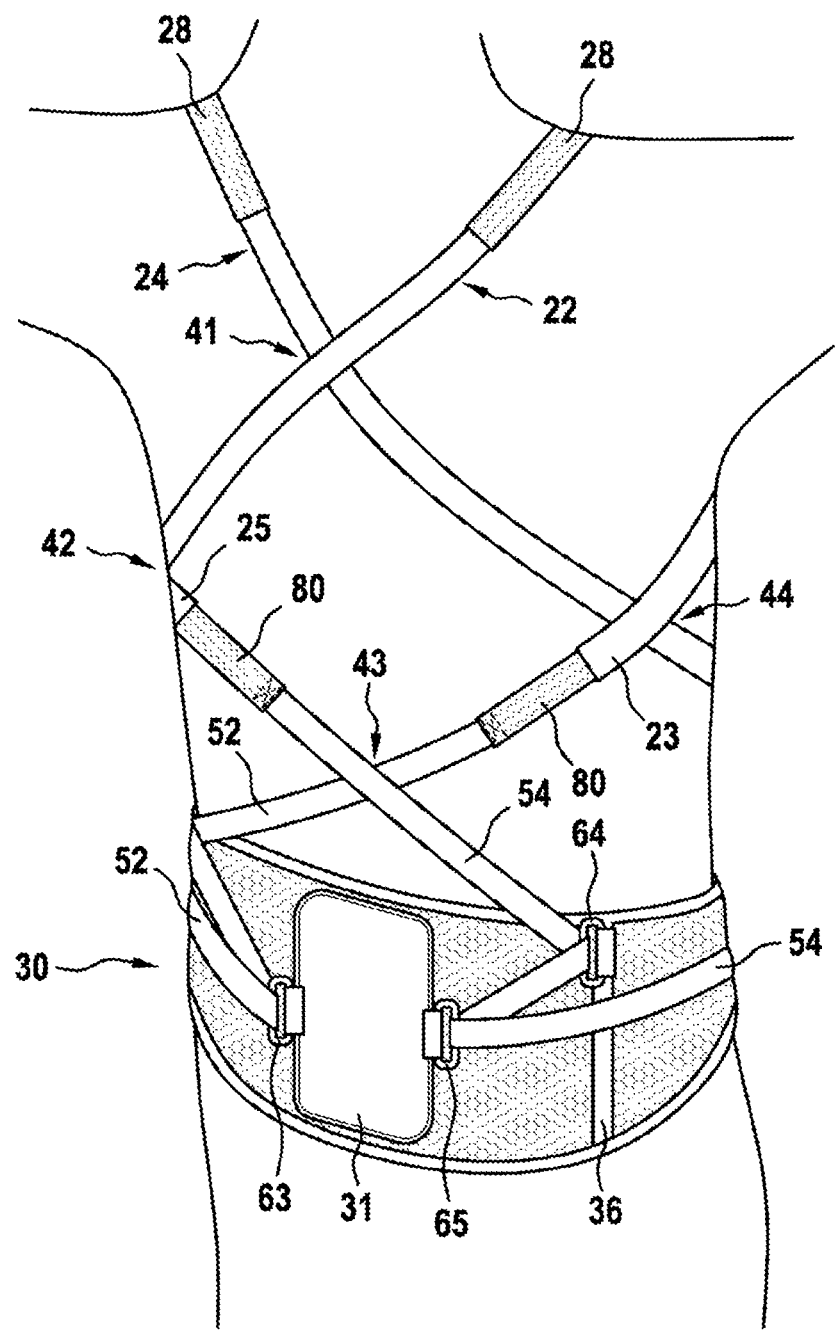

FIG. 3 is a perspective rear view of the back orthosis according to FIG. 2 in a form applied to a wearer. It is also shown that the first deflection elements 62, 64 are arranged in the region of the elastic pelvis strap 30 on a stiffening element 36 and particularly directly connected to it. The middle portion 31, designed as a stiffening element, of the pelvis strap 30, on which the second deflection elements 63, 65 are arranged and to which they are particularly directly connected, can also be seen.

Figure 4:
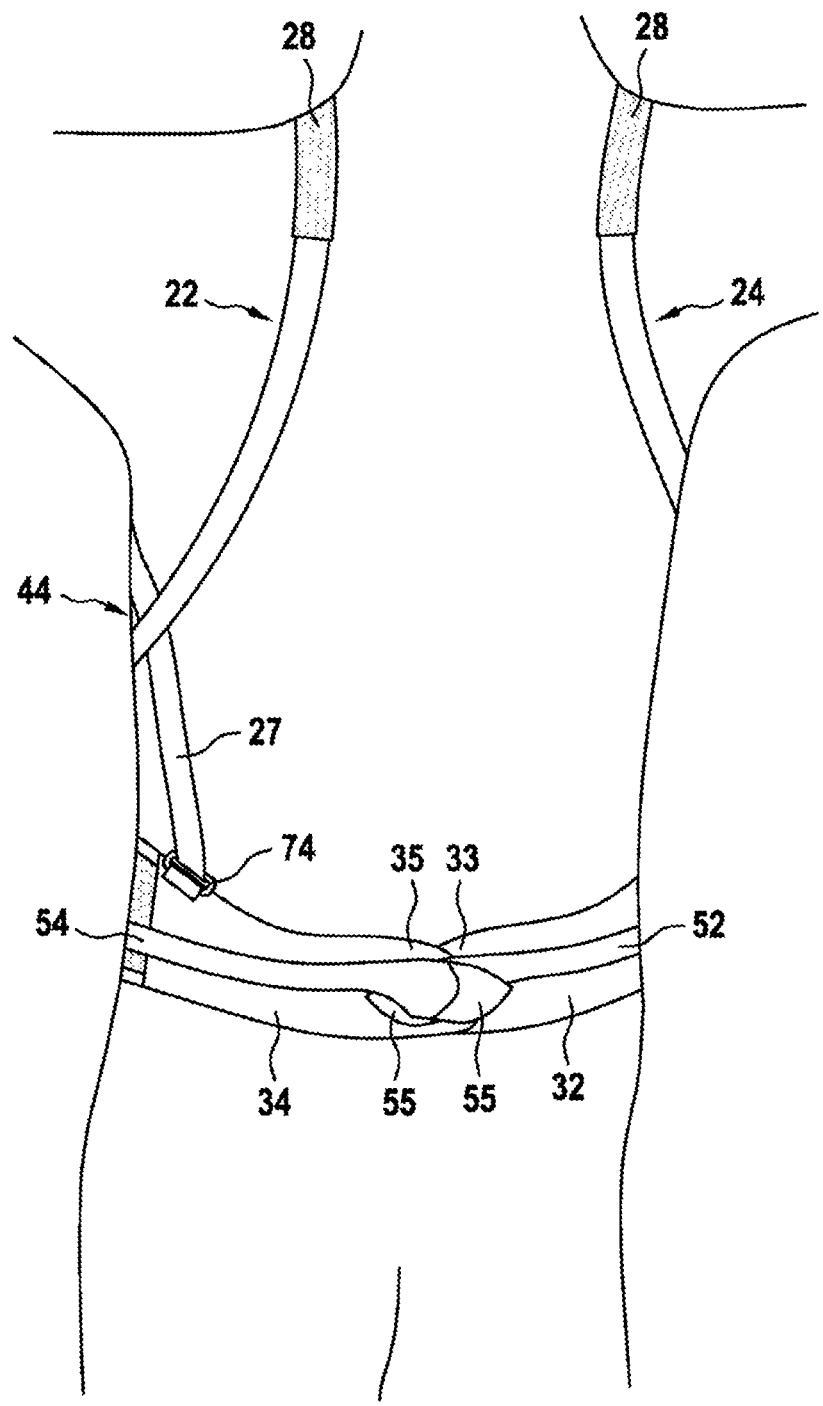

FIG. 4 is a perspective front view of the embodiment according to FIG. 1 in the state applied to the wearer; the reference signs apply accordingly.

Figure 5A:
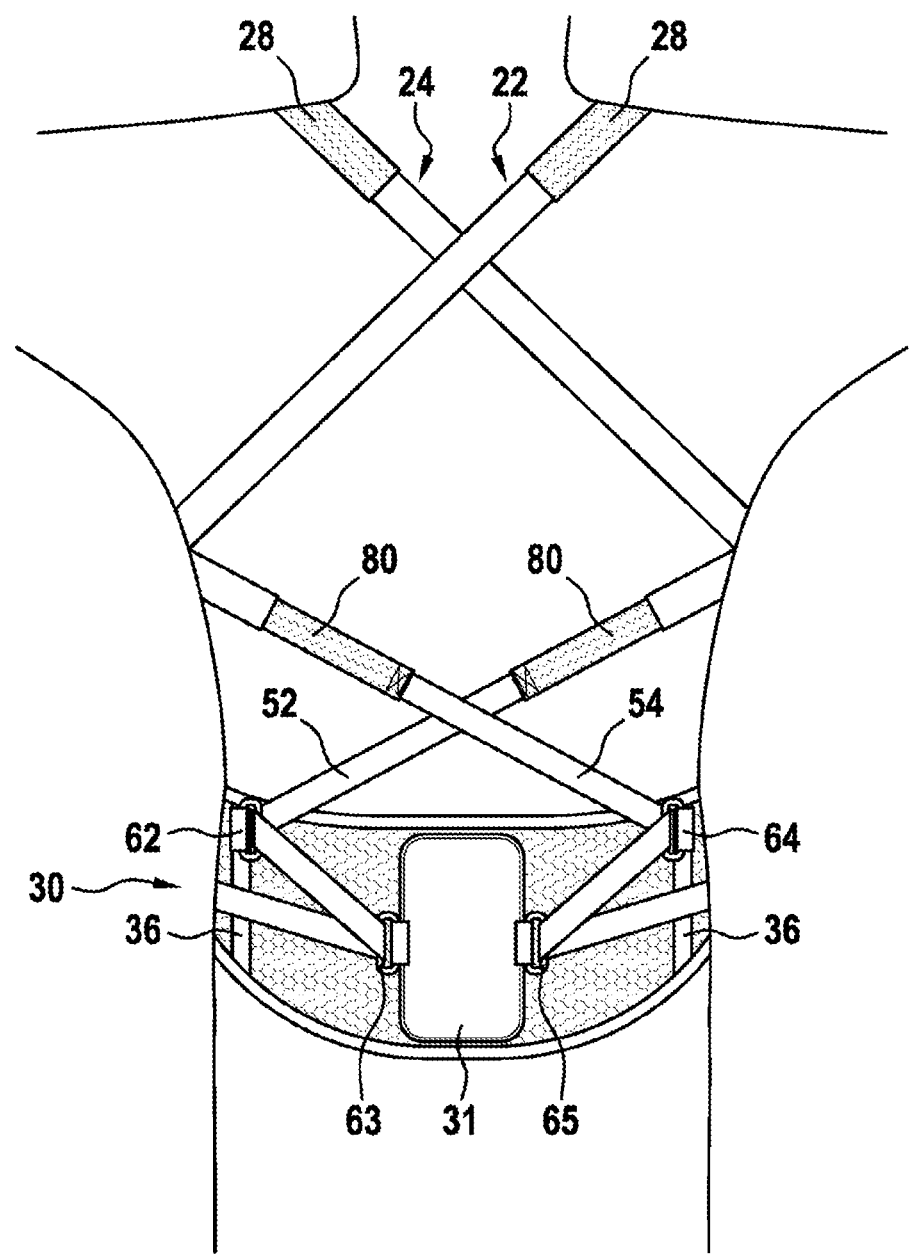
Figure 5B:
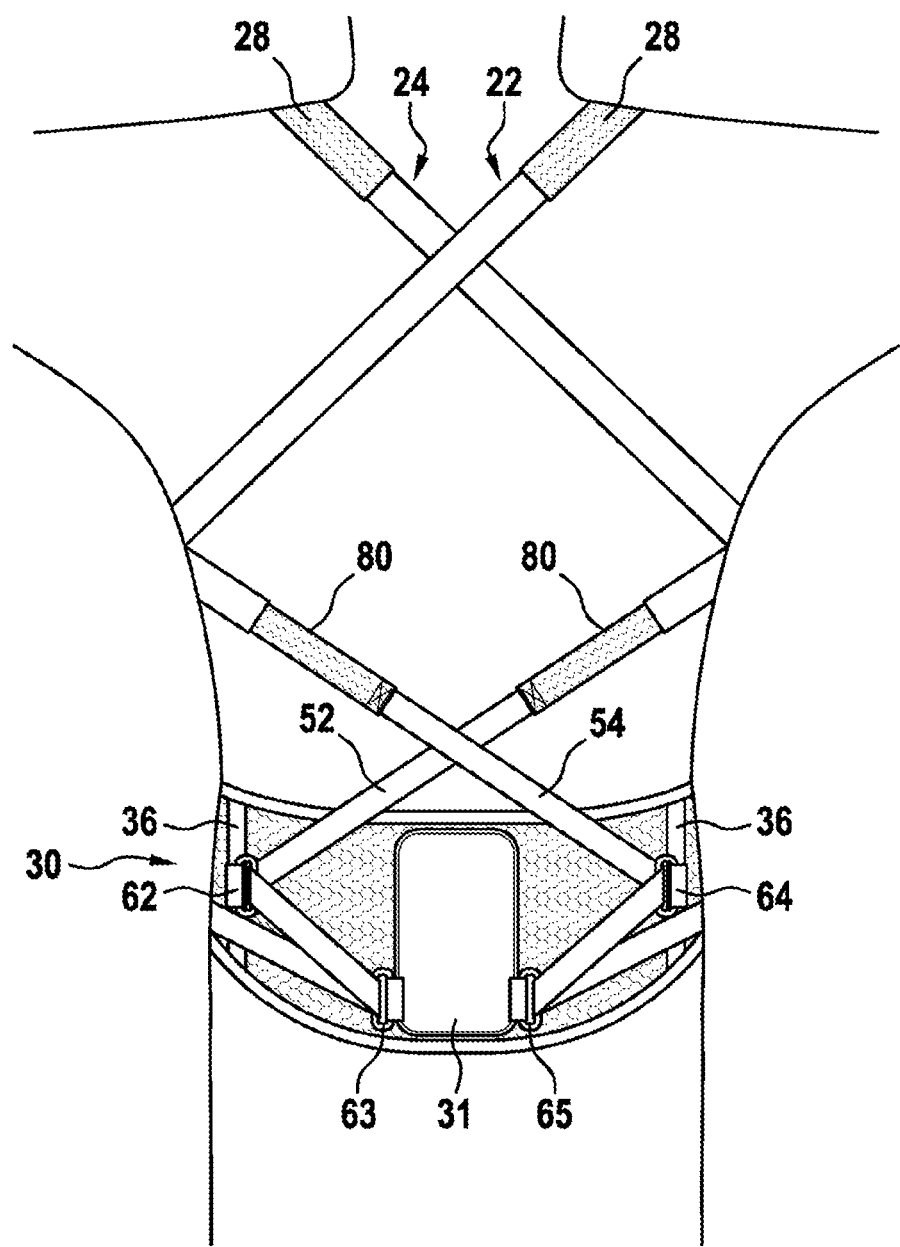

FIGS. 5A and 5B each show alternative variants of the embodiment according to FIG. 2 or 3, wherein the first deflection elements 62, 64 can be fixed or are fixed on the stiffening elements 36, and the second deflection elements 63, 65 can be fixed or are fixed to the middle portion 31 of the pelvis strap designed as a stiffening element in variable positions, resulting in an alternatively configured arrangement of the respective tension straps 52, 54 guided in said deflection elements on the pelvis strap 30. FIG. 5A shows a first arrangement of the first deflection elements 62 and 64 on the upper edge of the pelvis strap 30 and that of the second deflection elements 63, 65 at middle height on the middle portion 31. FIG. 5B shows an alternative arrangement of the first deflection elements 62, 64 in the central region of the pelvis strap 30 and that of the second deflection elements 63, 65 in the lower region of the middle portion 31.

Figure 6:
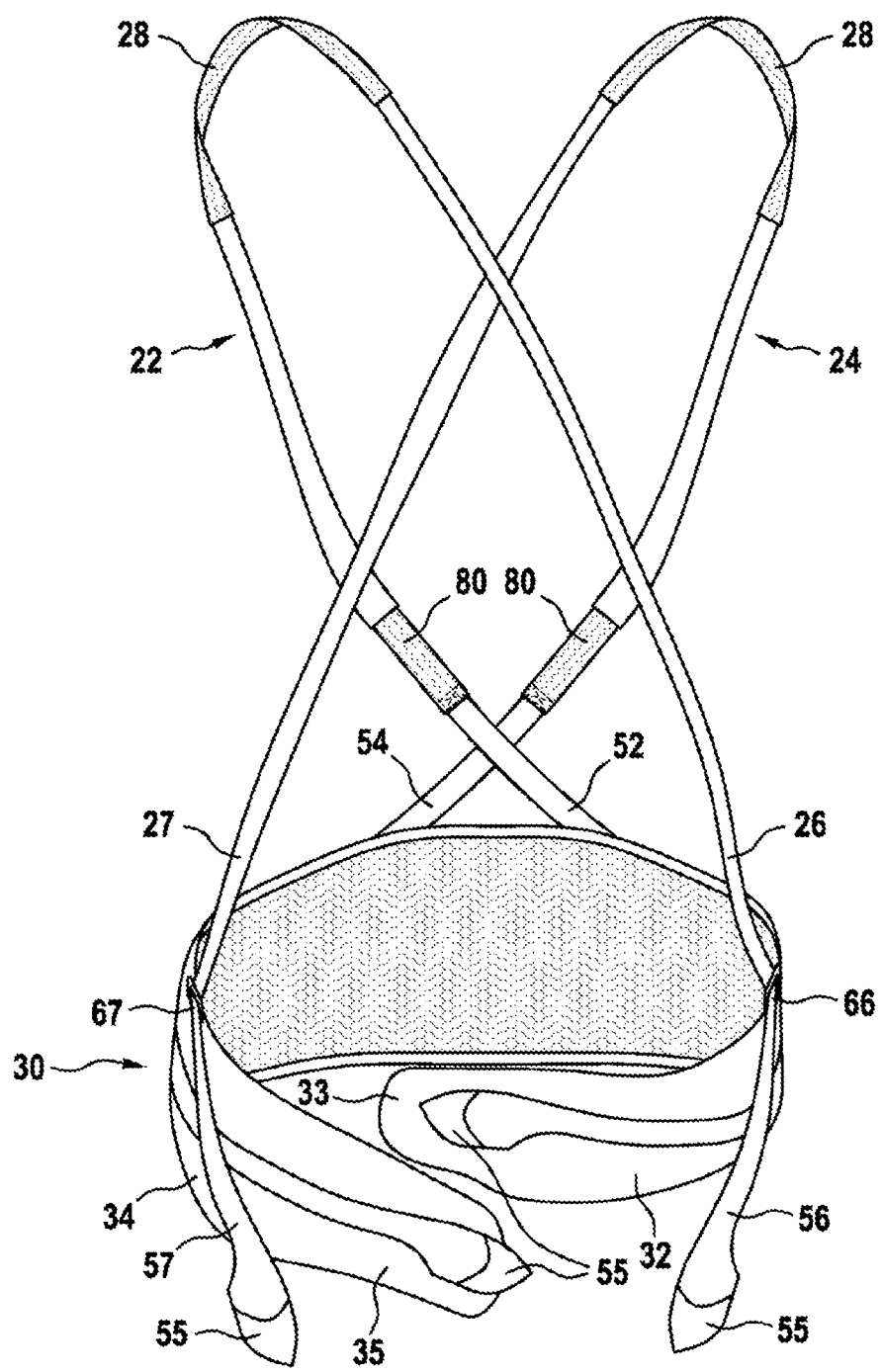

FIG. 6 shows a further alternative embodiment of the back orthosis in a front view analogous to the representation in FIG. 1. Deviating from the embodiments according to FIG. 1 and also from the alternative embodiment according to FIG. 2, in this depicted variant of said embodiments, it is additionally provided that the free second ends 26 and 27 of the two shoulder strap loops 22, 24 are each guided in left and right lateral deflection elements 66, 67, and wherein the second end 26 of the right shoulder strap loop 22 ends in a second tension strap 56 and the second end 27 of the left shoulder strap loop 24 ends in a second tension strap 57. They can also each be fixed to the left and right pelvis strap ends 33, 35 via their free tension strap ends 55. In this embodiment, both ends 23, 25, 26, 27 of the respective shoulder strap loops can thus be tensioned separately via individually assigned tension straps 52, 54, 56, 57.

Figure 7:
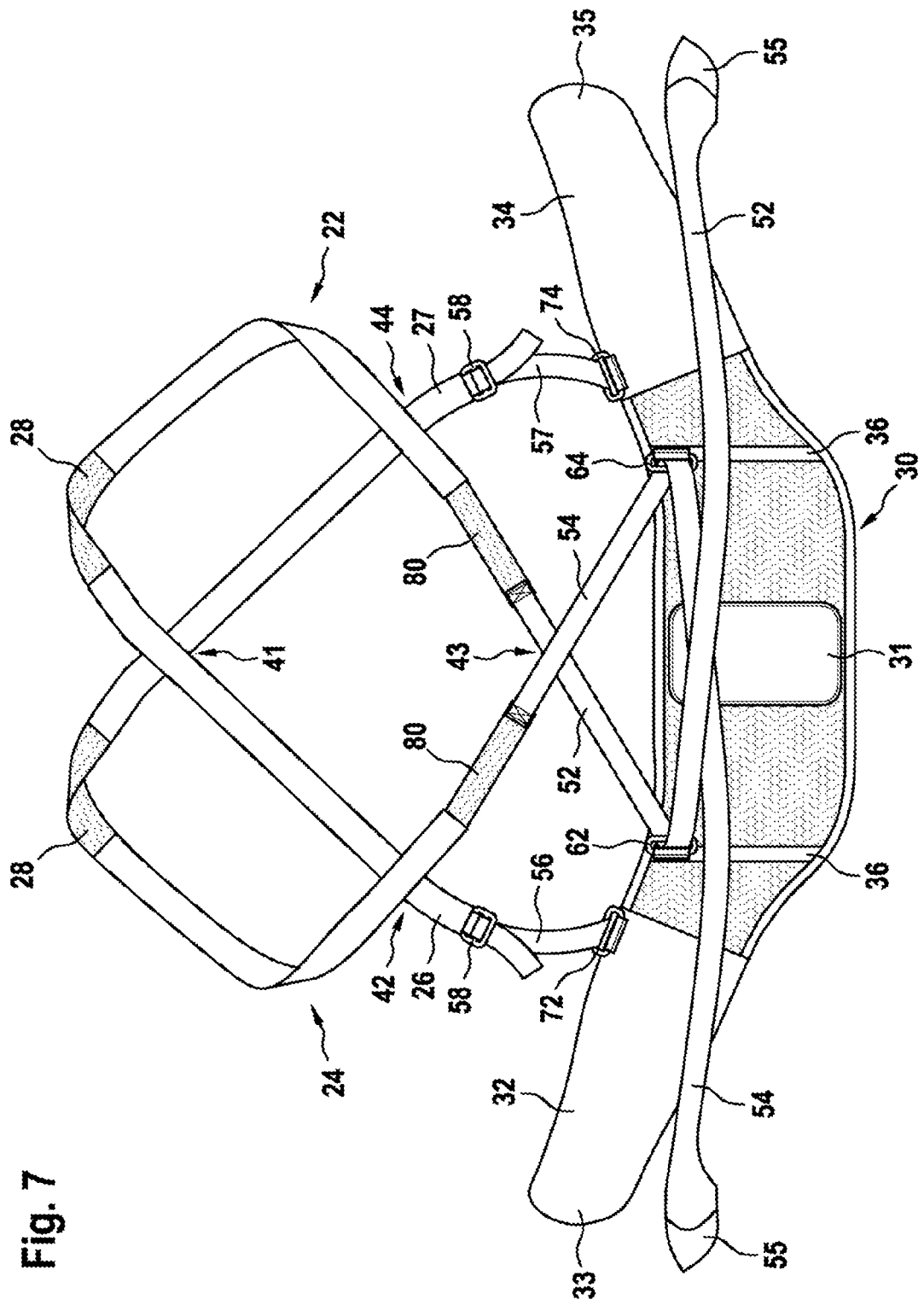

FIG. 7 shows a further embodiment of the back orthosis according to the invention according to FIG. 1 in a representation analogous to the representation in FIG. 2. The same reference signs denote the same or functionally identical elements.

Figure 8:
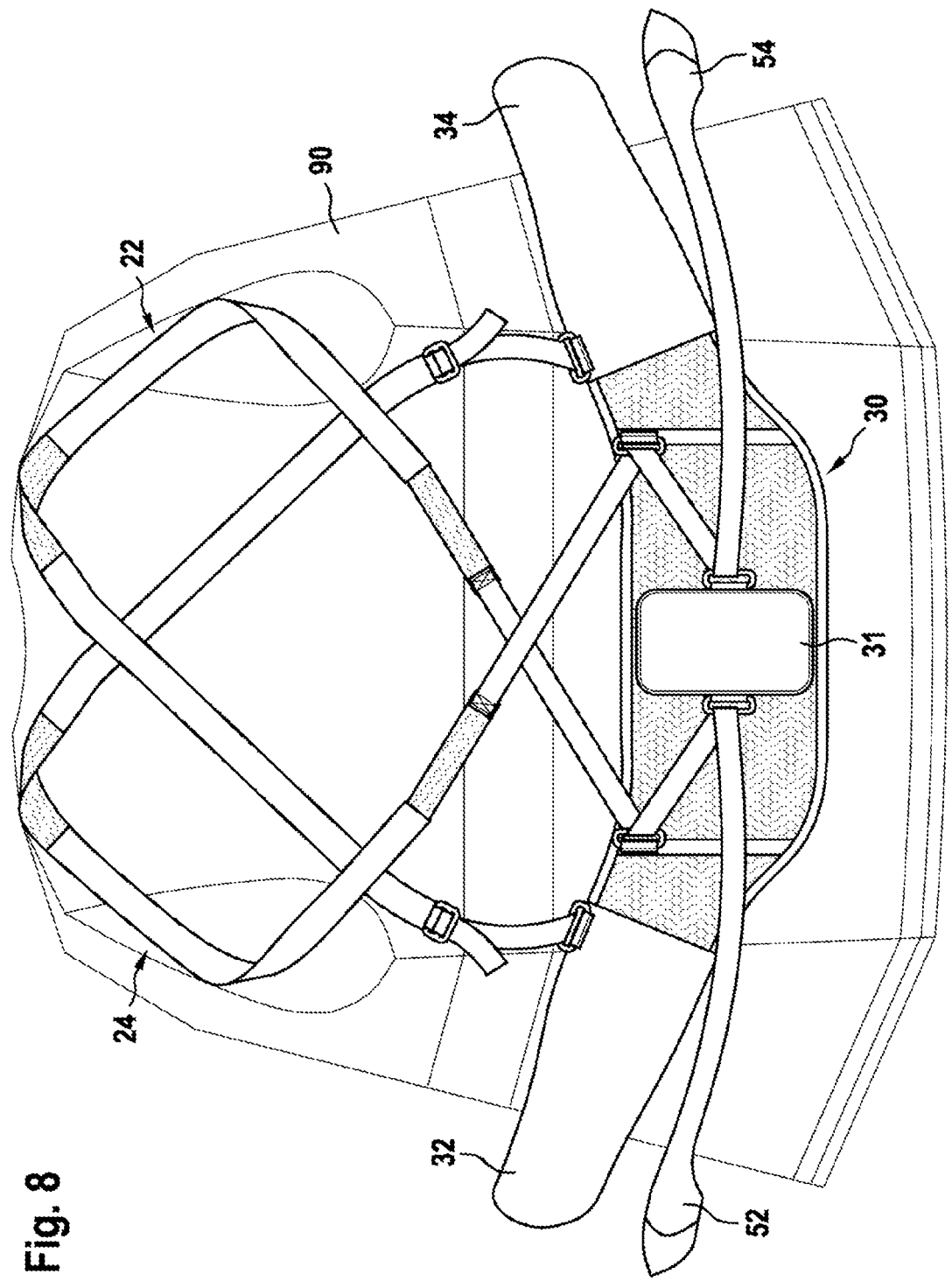

FIG. 8 shows a further embodiment of the invention as protective clothing: A back support belt system analogous to the embodiment according to FIG. 2 is fitted onto an elastic vest 90. At least in portions, the right and left shoulder strap loops 22, 24 and the pelvis strap 30 are firmly connected to the vest 90. The back orthosis can thus be applied directly and immediately together with the vest 90.

LIST OF REFERENCE SIGNS

Right shoulder strap loop (22)
The first end (23) of the right shoulder strap loop
Left shoulder strap loop (24)
The first end (25) of the left shoulder strap loop
The second end (26) of the right shoulder strap loop
The second end (27) of the left shoulder strap loop
Shoulder strap (28)
Pelvis strap (30)
Middle portion (31)
Left side portion (32)
Left pelvis strap end (33)
Right side portion (34)
Right pelvis strap end (35)
Stiffening element (36)
Central upper crossing point (41)
Left lateral crossing point (42)
Central lower crossing point (43)
Right lateral crossing point (44)
The first tension strap (52) of the right shoulder strap loop
The first tension strap (54) of the left shoulder strap loop
The second tension strap (56) of the right shoulder strap loop
The second tension strap (57) of the left shoulder strap loop
Belt buckle (58)
First left deflection element (62)
Second left deflection element (63)
First right deflection element (64)
Second right deflection element (65)
Left lateral deflection element (66)
Right lateral deflection element (67)
Left anchor (72)
Right anchor (74)
Elastic strap portion (80)
Jacket (90)

The invention claimed is:

1. A back orthosis comprising:
a stretchable pelvis strap (30) to be applied to the pelvis of a wearer, having a middle portion (31) that can be positioned in the lumbar/sacral region in the applied state and a left side portion (32) extending laterally therefrom with a left pelvis strap end (33) and a right side portion (34) extending laterally therefrom with a right pelvis strap end (35), wherein the pelvis strap ends (33, 35) are connectable to each other under tension for application,
a right shoulder strap loop (22) to be applied over the right shoulder of the wearer, which is connected via its first end (23) and its second end (26) to the left side portion (32) of the pelvis strap (30),
a left shoulder strap loop (24) to be applied over the left shoulder of the wearer, which is connected via its first end (25) and its second end (27) to the right side portion (34) of the pelvis strap (30),
a first elastic strap (80) connected to the first end (23) of the right shoulder strap loop (22);
a first inelastic strap (52) connected to the first elastic strap (80);
a first left deflection element (62) fastened to the first inelastic strap (52), the first inelastic strap (52) being configured to slide through the first left deflection element (62) in a tensioned state, the first inelastic strap (52) changing in orientation as the first inelastic strap (52) slides through the first left deflection element (62), the first left deflection element (62) connecting the first inelastic strap (52) to a left side of the stretchable pelvis strap (30);
a second elastic strap (80) connected to the first end (25) of the left shoulder strap loop (24);
a second inelastic strap (54) connected to the second elastic strap (80);
a first right deflection element (64) fastened to the second inelastic strap (54), the second inelastic strap (54) being configured to slide through the first right deflection element (64) in a tensioned state, the second inelastic strap (54) changing in orientation as the second inelastic strap (54) slides through the first right deflection element (64), the first right deflection element (64) connecting the second inelastic strap (54) to a right side of the stretchable pelvis strap (30).

2. The back orthosis according to claim 1, wherein the right shoulder strap loop (22) and the left shoulder strap loop (24) cross each other in the applied state in a dorsal central upper crossing point (41), in a dorsal central lower crossing point (43) in the applied state, and in two lateral crossing points (42, 44) in the applied state.

3. The back orthosis according to claim 1, wherein the tension straps (52, 54) each have a free tension strap end (55) which can be fixed directly to the respective pelvis strap ends (33, 35) for tensioning the tension straps (52, 54).

4. The back orthosis according to claim 1, wherein the shoulder strap loops (22, 24) can be tensioned via the tension straps (52, 54), which run on the side portions (32, 34) in a sliding manner and are fixed to the respective pelvis strap end (33, 35), via the stretching of the pelvis strap (30) when the back orthosis is applied and the pelvis strap (30) is closed.

5. The back orthosis according to claim 1, wherein the shoulder strap loops (22, 24) can be separately tensioned via the tension straps (52, 54) and can be fixed to the respective pelvis strap end (33, 35) when the back orthosis is in the applied state and the pelvis strap (30) is closed.

6. The back orthosis according to claim 1, wherein the closed pelvis strap (30) can additionally be tensioned further in the applied state of the back orthosis via the tension straps (52, 54) of the shoulder strap loops (22, 24).

7. The back orthosis according to claim 1, wherein the second end (26, 27) of the shoulder strap loops (22, 24) is each connected to the respective left and right side portions (32, 34) at left and right lateral anchors (72, 74), and wherein the left and right lateral anchors (72, 74) are located on or in the region of the left and right iliac crest (crista iliaca) of the wearer when the pelvis strap (30) is in the applied state.

8. The back orthosis according to claim 1, wherein at least one deflection element (62, 64, 63, 65, 66, 67) is formed separately and can be coupled to the pelvis strap (30) in a position-variable manner.

9. The back orthosis according to claim 1, wherein an elastic strap portion (80) is formed between one end of the shoulder strap loop (22, 24) and the tension strap (52, 54), the elasticity of said elastic strap portion (80) being higher than that of the shoulder strap loops (22, 24) themselves.

10. The back orthosis according to claim 9, wherein an additional expansion limiter in the form of at least one less elastic or inelastic strap portion guided in a parallel manner is formed on the elastic strap portion (82, 84).

11. A protective clothing, comprising a stretchable vest or jacket (90) and a back support belt system comprising the back orthosis of claim 1, wherein the shoulder strap loops (22, 24) and the pelvis strap (30) are fitted at least in portions onto the vest or the jacket (90) and firmly connected to the vest or the jacket.

12. A method for protecting against adverse stress on the back of a subject, comprising applying the back orthosis according to claim 1 on the back of the subject.

13. The back orthosis of claim 1, wherein the right shoulder strap loop (22) and the left shoulder strap loop (24) each comprise one or more elastic and padded segments (28).

14. The back orthosis of claim 1, wherein the left deflection element (62) and the right deflection element (64) each comprise vertically oriented grooves into which the first inelastic strap (52) and the second inelastic strap (54), respectively, slide.

15. The back orthosis of claim 14, wherein the left deflection element (62) and the right deflection element (64) are each directly connected to separate stiffening elements (36), the stiffening elements (36) being oriented vertically.

* * * * *